United States Patent [19]

Ishikawa et al.

[11] Patent Number: 4,544,747

[45] Date of Patent: Oct. 1, 1985

[54] QUINOLINE CARBOXYLIC ACID DERIVATIVES

[75] Inventors: Hiroshi Ishikawa; Fujio Tabasa; Kazuyuki Nakagawa, all of Tokushima, Japan

[73] Assignee: Otsuka Pharmaceutical Company, Limited, Japan

[21] Appl. No.: 604,574

[22] Filed: Apr. 27, 1984

Related U.S. Application Data

[63] Continuation of Ser. No. 342,200, Jan. 25, 1982, abandoned, which is a continuation of Ser. No. 123,256, Feb. 20, 1982, abandoned.

[30] Foreign Application Priority Data

Feb. 26, 1979 [JP] Japan .................. 54-22162

[51] Int. Cl.[4] .......................................... C07D 217/24
[52] U.S. Cl. ...................... 546/156; 544/363
[58] Field of Search .................. 546/156; 544/363

[56] References Cited

U.S. PATENT DOCUMENTS

| | | | |
|---|---|---|---|
| 3,849,421 | 11/1974 | Nakagome et al. | 546/156 |
| 4,017,622 | 4/1977 | Minami et al. | 544/363 |
| 4,146,719 | 3/1979 | Irikura et al. | 544/363 |
| 4,448,962 | 5/1984 | Irikura et al. | 544/384 |

FOREIGN PATENT DOCUMENTS

| | | | |
|---|---|---|---|
| 1141383 | 2/1983 | Canada | 544/363 |
| 2246503 | 4/1974 | Fed. Rep. of Germany | 546/156 |
| 2554772 | 6/1976 | Fed. Rep. of Germany | 546/156 |
| 51-88973 | 1/1976 | Japan . | |
| 54-14978 | 3/1979 | Japan . | |
| 56-128703 | 10/1981 | Japan | 544/363 |
| 830832 | 3/1960 | United Kingdom . | |
| 2034698 | 6/1980 | United Kingdom | 544/363 |

*Primary Examiner*—Glennon H. Hollrah
*Assistant Examiner*—James H. Turnipseed
*Attorney, Agent, or Firm*—Larson and Taylor

[57] ABSTRACT

A quinoline carboxylic acid derivative of the general formula

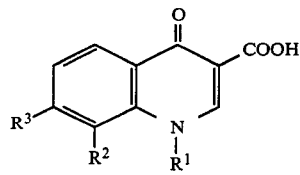

[wherein $R^1$ and $R^2$ are a lower alkyl group, respectively, and $R^3$ is a halogen atom or 1-piperazinyl group] and its salt are of value as an antimicrobial agent for medical treatment and agricultural and horticultural uses.

3 Claims, No Drawings

QUINOLINE CARBOXYLIC ACID DERIVATIVES

This is a continuation of application Ser. No. 342,200 filed 1/25/82 which is a continuation of Ser. No. 123,256, filed 2/20/80 both now abandoned.

This invention relates to novel quinoline carboxylic acid derivatives.

The compounds of this invention are novel compounds which have not been described in the literature, and comprise quinoline carboxylic acid derivatives represented by the general formula (1) and their salts:

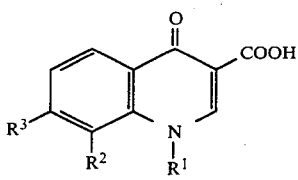

[wherein $R^1$ and $R^2$ each designate a lower alkyl group; and, $R^3$ is a halogen atom or 1-piperazinyl group].

The compounds of this invention are useful as antimicrobial agents for medical treatment and agricultural-horticultural uses.

Referring to the general formula (1) described above, as examples of the alkyl group designated by $R^1$ and $R^2$ may be mentioned a straight-chain or branched-chain alkyl group having 1 to 4 carbon atoms, being specifically exemplified by methyl, ethyl, propyl, isopropyl, butyl, tert-butyl and so forth; and, as the halogen atom designated by $R^3$ may be specifically mentioned fluorine, chlorine, bromine and iodine.

As representative compounds according to this invention may be mentioned:

1-Ethyl-7-(1-piperazinyl)-8-methyl-4-oxo-1,4-dihydroquinoline-3-carboxylic acid
1,8-Dimethyl-7-(1-piperazinyl)-4-oxo-1,4-dihydroquinoline-3-carboxylic acid;
1,8-Diethyl-7-(1-piperazinyl)-4-oxo-1,4-dihydroquinoline-3-carboxylic acid;
1-Ethyl-8-butyl-7-(1-piperazinyl)-4-oxo-1,4-dihydroquinoline-3-carboxylic acid;
1-Butyl-8-methyl-7-(1-piperazinyl)-4-oxo-1,4-dihydroquinoline-3-carboxylic acid;
1-Isopropyl-8-methyl-7-(1-piperazinyl)-4-oxo-1,4-dihydroquinoline-3-carboxylic acid;
1-Ethyl-7-chloro-8-methyl-4-oxo-1,4-dihydroquinoline-3-carboxylic acid;
1,8-Diethyl-7-chloro-4-oxo-1,4-dihydroquinoline-3-carboxylic acid;
1-Ethyl-7-fluoro-8-methyl-4-oxo-1,4-dihydroquinoline-3-carboxylic acid;
1-Methyl-7-chloro-8-isopropyl-4-oxo-1,4-dihydroquinoline-3-carboxylic acid;
1-Ethyl-7-chloro-8-isoporpyl-4-oxo-1,4-dihydroquinoline-3-carboxylic acid;
1,8-Dimethyl-7-bromo-4-oxo-1,4-dihydroquinoline-3-carboxylic acid;

Among the compounds of the general formula (1) described above, preferred are the quinoline carboxylic acid derivatives wherein $R^1$ is ethyl, $R^2$ is a lower alkyl, and $R^3$ is chlorine, Fluorine or 1-piperazinyl group. The particularly preferable compounds according to this invention are 1-ethyl-7-chloro-8-methyl-4-oxo-1,4-dihydroquinoline-3-carboxylic acid, 1-ethyl-7-fluoro-8-methyl-4-oxo-1,4-dihydroquinoline-3carboxylic acid, and 1-ethyl-7-(1-piperazinyl)-8-methyl-4-oxo-1,4-dihydroquinoline-3-carboxylic acid.

The compound of this invention may be produced by various procedures, and as a representative procedure may be mentioned the one illustrated in the following reaction-step equation:

Reaction-step equation 1:

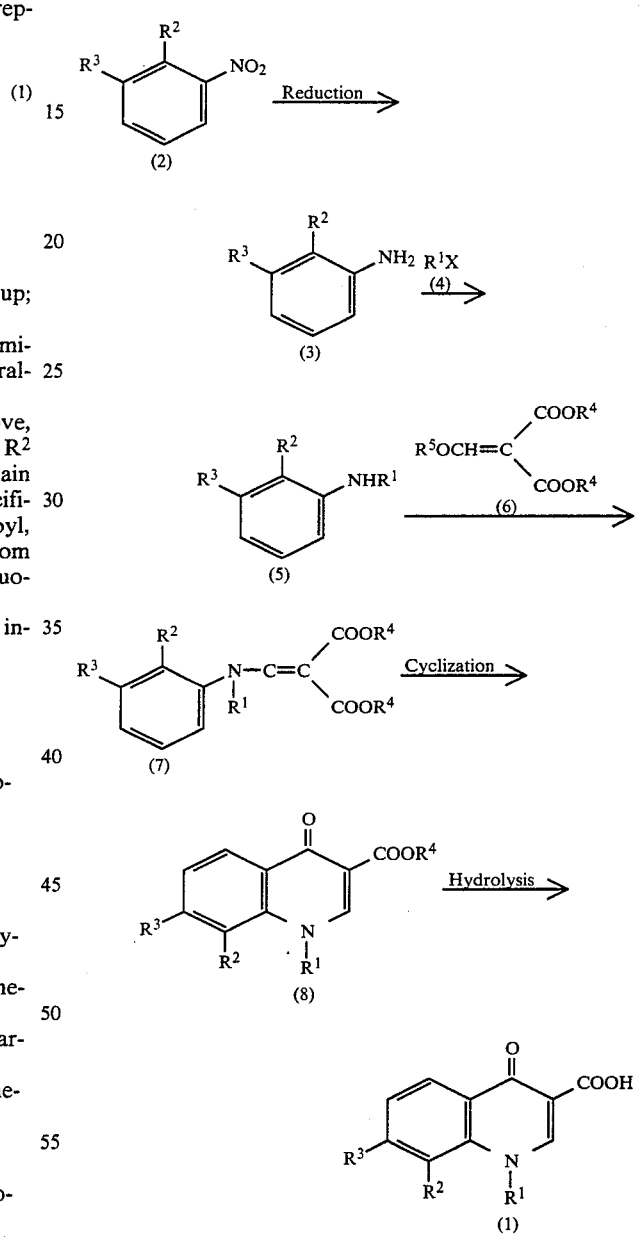

[wherein $R^1$, $R^2$ and $R^3$ are as defined above; $R^4$ and $R^5$, each, are a lower alkyl group; X means a halogen atom].

The compound (1b) of this invention wherein $R^3$ is 1-piperazinyl, as hereinafter described, is obtained also by reaction of the corresponding compound (1a) of this invention wherein $R^3$ is a halogen atom with piperazine.

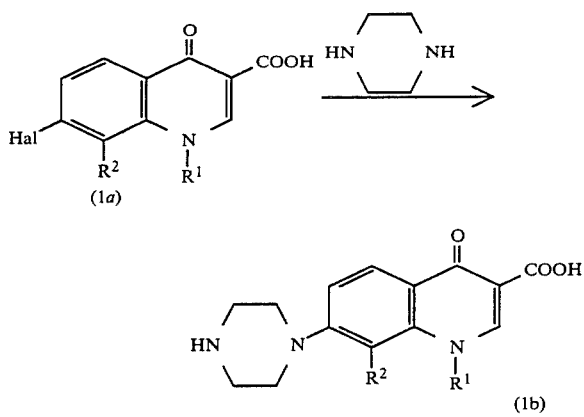

[wherein Hal designates a halogen atom; and, $R^1$ and $R^2$ are as defined above].

As a means of reducing the known nitrobenzene derivative designated by the general formula (2) may be mentioned a procedure with the use of a reducing agent, a procedure through catalytic reduction, and so forth. In the event the procedure with the use of a reducing agent is adopted, such reducing agent to be utilized may be exemplified by iron-hydrochloric acid, zinc-acetic acid, stannous chloridehydrochloric acid, and the like. The quantities in which the reducing agent is utilized are normally equimolar to excessive against the compound of the general formula (2) and, preferably, about 3 to 5 times molar ones. Said reduction reaction is carried out, normally, in the range of room temperature to 150° C. and, preferably, in the range of about 50° to 100° C., and usually goes to completion within the range of about 30 minutes to 3 hours. In this manner, there is produced the compound of the general formula (3).

In the reaction of the compound of the general formula (3) with the compound of the general formula (4), the proportion in which both are used may better be, normally, in not less than equimolar quantity of the latter against the former and, preferably, not less than double the molar quantity. Said reaction is normally conducted in the presence of a basic compound, without a solvent or in an inert solvent. The basic compound may be exemplified by hydroxides of alkali metals such as sodium hydroxide and potassium hydroxide, inorganic carbonates such as sodium carbonate, potassium carbonate, potassium hydrogencarbonate and sodium hydrogencarbonate, tertiary amines such as pyridine, quinoline, triethylamine and tributylamine, and so forth. It is preferable to use such basic compound in the quantities not less than equimolar with, and preferably, 1.1 to 1.5 times molar of, the compound of the general formula (3). The solvent that is utilizable may be exemplified by lower alcohols such as methanol, ethanol and isopropanol, ethers such as dioxane, tetrahydrofuran and diglyme, aromatic hydrocarbons such as benzene and toluene, dimethylsulfoxide, diemthylformamide, hexamethylphosphoric acid triamide, pyridine, and so forth. Among these, preferable are aromatic hydrocarbons. Said reaction is carried out normally at a temperature of room temperature to 150° C., and preferably at a temperature of about 80° to 130° C., and usually goes to completion in about 0.5 to 6 hours. In this manner, there is produced the compound of the general formula (5).

A reaction of the compound of the general formula (5) with the compound of the general formula (6) is carried out without a solvent or in a solvent such as methanol, ethanol, isopropanol, acetonitrile, dimethylformamide, dimethylsulfoxide, and hexamethylphosphoramide, and preferably without a solvent. The proportion in which the compound (6) is used against the compound (5) may be usually equimolar or more and, preferably, equimolar in the case of the reaction without a solvent and is about 1.1 to 1.5 times molar quantity in the case of the reaction in the presence of a solvent. The reaction temperature is normally in the range of room temperature to 150° C. and preferably in the range of about 100° to 130° C., and the reaction normally goes to completion in about 0.5 to 6 hours, resulting readily in production of the compound represented by the general formula (7).

The cyclization reaction of the compound (7) obtained in this way may be conducted in accordance with various cyclization reactions conventional per se. Such cyclizations may be exemplified by a procedure by means of heating, a procedure with the use of such an acidic substance as phosphorus oxychloride, phosphorus pentachloride, phosphorus trichloride, thionyl chloride, concentrated sulfuric acid and polyphosphoric acid, and the like. Where the cyclization procedure by means of heating is adopted, a solvent such as high-boiling hydrocarbons and high-boiling ethers, e.g. tetralin, diphenyl ether and diethylene glycol dimethyl ether may be used, while the heating condition, usually at about 100° to 250° C. and preferably at about 150° to 200° C., is employable. Where the cyclization procedure with the use of an acidic substance is adopted, it is suggested that such acidic substance is used in the proportion ranging from the equimolar amount to a large excess against the compound (7) and, preferably about 10 to 20 times the amount, to allow the reaction to proceed at a temperature of about 100° to 150° C. for about 0.5 to 6 hours. In this manner, there is produced the compound of the general formula (8).

The hydrolysis reaction of the compound (8) obtained by the above-mentioned cyclization reaction is carried out by the conventional procedures, for example, in the presence of conventional catalysts such as basic compounds, e.g., sodium hydroxide, potassium hydroxide and barium hydroxide, mineral acids, e.g., sulfuric acid, hydrochloric acid and nitric acid, and organic acids, e.g., acetic acid and aromatic sulfonic acid. Said reaction is generally conducted in a usually employed solvent such as water, methanol, ethanol, isopropanol, acetone, methyl ethyl ketone, dioxane, ethylene glycol and acetic acid. The reaction temperature is normally in the range of room temperature to 200° C. and preferably in the range of about 50° to 150° C. By the above procedures, there is easily obtained the objective compound of this invention represented by the general formula (1).

Referring then to the reaction between the compound of the general formula (1a) and piperazine, the proportion in which such compounds are used are not specifically restricted and may be selected in a wide range; it is advisable to use, against the former, usually not less than the equimolar quantity of the latter, and preferably the equimolar to five times molar quantity. Said reaction is carried out in an inert solvent. Such solvent may be exemplified by water, alcohols such as methanol, ethanol, isopropanol, butanol, amyl alcohol and cyclohexyl alcohol, aromatic hydrocarbons such as benzene, toluene and xylene, ethers such as tetrahydrofuran, dioxane and diglyme, dimethylsulfoxide, dimethylformamide, hexamethylphosphoric acid triamide, etc. Among others, preferred are dimethylsulfoxide, dimethylformamide and hexamethylphosphoric acid triamide. Said reaction may be carried out in the presence of a deacidifying agent. Such deacidifying agent may be exemplified by inorganic carbonates such as sodium carbonate, potassium carbonate, potassium hydrogencarbonate and sodium hydrogencarbonate, tertiary amines such as pyridine, quinoline and triethylamine, and the like. Said reaction is conducted under the pressure of, normally about 1 to 20 atmospheric pressure and preferably about 1 to 10 atmospheric pressure, at a temperature of, normally about 100° to 250° C. and preferably about 140° to 200° C., and generally goes to completion within the time range of about 5 to 20 hours. By the above procedure, there is produced the compound of this invention represented by the general formula (1) wherein $R^3$ is 1-piperazinyl (the compound of the general formula (1b)).

Included in the present invention are both acid addition and carboxylic acid salts of the quinoline carboxylic acid of the general formula (1) obtained in the above-mentioned manner.

The acid which is useful for formation of the acid addition salts may be various kinds of pharmacologically or agrochemically acceptable organic or inorganic acids, being exemplified by inorganic acids such as hydrochloric acid, sulfuric acid, nitric acid, hydrobromic acid and phosphoric acid, and organic acids such as acetic acid, oxalic acid, malonic acid, succinic acid, maleic acid, fumaric acid, malic acid, mandelic acid, ethane sulfonic acid and p-tosyl acid.

The basic compound which is used for formation of the carboxylic acid salts may be various kinds of pharmacologically or agrochemically acceptable basic compounds, being exemplified by inorganic, basic compounds such as sodium hydroxide, potassium hydroxide, calcium hydroxide, aluminium hydroxide and sodium hydrogencarbonate, and the like.

The compound of this invention produced in this manner can be easily separated and purified by conventionally employed separation means, after completion of the reaction steps hereinbefore described. As the separation means, there may be mentioned, by way of example, the solvent extraction procedure, dilution procedure, precipitation procedure, recrystallization procedure, column chromatography, preparative thin-layer chromatography, and so forth.

The compounds of this invention as represented by the general formula (1) and their salts are low in toxicity while they have the excellent antimicrobial activity and, are useful as an antimicrobial agent. The antimicrobial agent according to the present invention is of value in the prevention and treatment of diseases of animals and agricultural and horticultural products caused by bacteria and fungi. As the animals may be mentioned mammals including man, birds, fishes and the like. The antimicrobial agent according to the present invention is also of use in the sterilization and disinfection of medical equipment and instruments, etc. and, in the events where agricultural and horticultural products are anticipated to be susceptible to damage by bacteria and fungi during storage and transit, can prevent such damage by applying in advance on such products by spreading, spraying, coating, etc. Consequently, the compounds of this invention and their salts are of value as an antimicrobial agent for medical treatment and agricultural-horticultural uses.

The antimicrobial agent according to this invention is effective against both gram-positive and gram-negative bacteria, and as examples of such bacteria may be mentioned Pseudomonadaceae such as Pseudomonas and Xanthomonas; Enterobacteriaceae such as Erwinia, Escherichia, Klebsiella, Serratia, Proteus, Salmonella, Shigella, etc.; Micrococcaceae such as Staphylococcus; Lactobacillaceae such as Streptococcus, and so forth. The antimicrobial agent according to the present invention shows the excellent antimicrobial activity against, among others, Erwinia, Xanthomonas, Pseudomonas and Streptococcus, and especially, demonstrates the exceedingly superior effect as the antimicrobial agent against Erwinia and Xanthomonas.

As examples of fungi causing the mycosis of animals, there may be mentioned *Cryptococcus neoformans, Coccidioides immites, Candida albicans, Aspergillus fumigatus*, etc.

Examples of fungi causing the mycosis of agricultural and horticultural products may include *Pyridularia oryzae, Helminthosporium oryzae, Helminthosporium sigmoideum, Phytophthora melonis, Phytophthora capsici, Phytophthora infestans, Colletotrichum lagenarium, Colletotrichum indicum, Sclerotinia sclerotiorum, Mycosphaerella melonis, Mycosphaerella phaseolicola, Alternaria solani*, etc.

The antimicrobial agent according to the present invention is useful in the prevention and treatment of bacteriosis and mycosis of animals and agricultural and horticultural products.

As examples of the bacteriosis of agricultural and horticultural products, there may be mentioned soft rot of vegetable, bacteria blight of rice, sheath blight of rice, peach bacterial spot, citrus canker, bacterial wilt of eggplant, bacterial wilt of tomato, fusarium wilt of tomato, fusarium wilt of watermelon, angular leaf spot of cucumber, and the like, while as the mycosis of agricultural and horticultural products there may be mentioned rice blast disease, helminthosporium leaf spot, late blight of cucumber, leaf blight of cucumber, anthracnose of cucumber, stem rot of eggplant, gummy stem blight of melon, early blight of tomato and the like. The antimicrobial agent according to the present invention exhibits the by far improved effect, especially, against soft rot of vegetable, as compared with conventional agents.

The antimicrobial agent for medical treatment uses according to the present invention has the excellent effect compared with antimicrobial agents containing nalidixic acid employed conventionally in this field, as may be clear from the antimicrobial-activity test 1 described hereinafter. In addition, the antimicrobial agent for agricultural and horticultural uses according to the present invention shows the excellent effect, as well, in comparison with the antimicrobial agents containing Streptomycin being conventionally employed, as may be apparent from the antimicrobial-activity test 2 described hereinafter.

The compounds of this invention, when they are intended for use as an antimicrobial agent for medical treatment uses, are normally formulated into the form of pharmaceutical preparation compositions in combination with preparative carriers for medical treatment uses. As the carriers may be mentioned, by way of example, diluents and excipients such as filler, extender, binder, wetting agent, disintegrator, surfactant and glazing agent.

As to the dosage form for such antimicrobial agent, various kinds of the forms may be selected in accordance with the intended purpose of treatment, and as their representatives may be mentioned, for example, the tablets, pills, powders, solutions, suspensions, granules, capsules, suppositories, injections (solutions, suspensions, etc.), ointments, etc. In forming into the form of tablets, extensive use may be made of carriers conventionally known in this field, being exemplified by excipients such as lactose, white sugar, sodium chloride, glucose solution, urea, starch, calcium carbonate, kaolin, crystalline cellulose and silicic acid, binders such as water, ethanol, propanol, syrup, glucose, starch solution, gelatin solution, carboxymethylcellulose, shellac, methylcellulose, potassium phosphate and polyvinylpyrrolidone, disintegrators such as dried starch, sodium alginate, agar powder, laminaria powder, sodium hydrogencarbonate, calcium carbonate, Tween, sodium lauryl sulfate, glyceryl monostearate, starch and lactose, disintegration suppressants such as white sugar, stearin, cacao butter and hydrogenated oils, absorption promoters such as quarternary ammonium salt and sodium lauryl sulfate, humectants such as glycerol and starch, adsorbents such as starch, lactose, kaolin, bentonite and colloidal silicic acid, glazing agent such as purified talc, stearic acid salts, boric acid powders and polyethylene glycol, and the like.

In forming into the form of pills, extensive use may be made of the carriers conventionally known in this field, being exemplified by excipients such as glucose, lactose, starch, cacao fats, hardened oils of plant origin, kaolin and talc, binders such as gum arabic powder, tragacanth powder, gelatin and ethanol, disintegrators such as laminaria and agar, and so forth. The tablets, further, as occasion demands, may be formed into tablets provided with usual coating films, such as sugar-coated, gelatin-coated, enteric-coated, film-coating or double-layer and multiple-layer tablets.

In forming into the form of suppositories, the conventionally known carriers are widely utilizable, and as such carriers may be mentioned, by way of example, polyethylene glycol, cacao fats, higher alcohol, esters of higher alcohols, gelatin, and semi-synthetic glycerides. In preparing as injections, the solutions and suspensions are desirably sterilized and isotonic with the blood, whereby, in forming into the forms of solutions, emulsions and suspensions, use may be made of any of the diluents conventionally employed in this field.

As examples of such diluent there may be mentioned water, ethyl alcohol, propylene glycol, ethoxylated isostearyl alcohol, polyoxyisostearyl alcohol, polyoxyethylene sorbit, sorbitan esters, and the like. In this case, sodium chloride, glucose or glycerol of a sufficient amount enough to prepare the isotonic solutions may be incorporated in an antimicrobial agent, whereby usual solubilizing agent, buffers, analgesia inducing agent, preservatives and the like may also be incorporated. Additionally, allowed to be contained in the antimicrobial agent of this invention, at need, may be coloring agent, preservatives, perfume, flavoring agent, sweetening agent and the like as well as other kinds of pharmaceuticals. In forming into the forms of pastes, creams and gels, wide use may be made of the diluents conventionally known in this field, being exemplified by white petrolatum, paraffin, cellulose derivatives, polyethylene glycol, silicone, bentonite and so forth.

The amount of the compound of this invention to be contained in the antimicorbial agent is not specifically restricted, being appropriately selected over a wide range, and may preferably be about 1 to 70% by weight of the total composition.

The above-mentioned antimicorbial agent is not specifically restricted in the mode of administration and may be formulated in various dosage forms; for example, tablets, pills, solution preparations, suspensions, emulsions, granules and capsules are administered orally; injections are given intravenously, solely or in conjunction with usual auxiliary solutions such as glucose and amino acids, while they, as the case may be, are solely administered intramuscularly, intradermally, subcutaneously or intraperitoneally; and, suppositories are given into the rectum, while ointments are directly applied.

Dosage of the compound of this invention, when being intended for use as an antimicrobial agent for medical treatment uses, is selected appropriately depending upon the application purposes, symptoms, etc., and it may be normally administered in a daily dosage of about 10 mg to 5 g/body, divided in 3 to 4 doses.

In addition, the compounds of this invention, in employing as an antimicrobial agent for agricultural-horticultural uses, may be formulated, in the same manner as the per se known antimicrobial agents for agricultural-horticultural uses with the use of such suitable carriers as the case may be, for example, a solid carrier, a liquid carrier, suspending agent and spreader, into any form such as granules, powders, dispersant, wettable powder, tablets, oil preparations, spray, aerosol, etc. Examples of the carrier which may be usable include clay, kaolin, bentonite, talc, acid clay, diatomaceous earth, calcium carbonate, nitrocellulose, starch, gum arabic, carbon dioxide gas, Freon, water, benzene, kerosene, alcohol, acetone, xylene, methylnaphthalene, cyclohexanone, esters of fatty acids of plant and animal origins, and so forth. The suspending agent and spreader may be exemplified by usual surfactants such as soap, esters of higher alcohols with sufuric acid, alkyl sulfonates, quarternary ammonium salts, polyalkylene oxide, etc.

The amount of the compound of this invention to be formulated in the preparations produced by the above procedures may be appropriately determined in accordance with their intended application forms, etc. For example, it is preferably in the range of about 0.1 to 90% by weight in formulating into the forms of the dispersant, wettable powder and the like, while it is suitably within the range of about 0.1 to 10% by weight for the forms of the powders, oil preparation and so forth.

The antimicrobial agent for agricultural-horticultural uses according to this invention, in putting into practical use, may be applied by spreading, spraying, coating, etc. on the spots where the antimicrobial effect is expected, just like the agricultural-horticultural, antimicrobial agents conventional per se. The application amounts may be determined in accordance with the required extent and degree of the antimicrobial effect. As the measure may desirably be taken such an application rate as the quantity of the effective component may be normally about 0.1 to 10 kg per hectare and preferably in the range of about 0.1 to 1 kg per hectare, although it may be varied depending upon the plant species and extent of plant damage. The antimicrobial agent, furthermore, may be used in conjunction with other kinds of antimicrobial agents insecticides, herbicides, fertilizer materials, soil conditioner or soil improving agent, and the like.

Described below are the examples for producing the starting materials according to this invention in Reference Examples, and the examples for preparing the compounds of this invention in Examples, together with the preparation examples.

REFERENCE EXAMPLE 1

Synthesis of 2-methyl-3-chloroaniline

To a mixed solution of 150 g of stannous chloride and 200 ml of concentrated sulfuric acid under ice-cooling is added 29 g of 2-chloro-6-nitrotoluene. Then, the solution is heated at 100° C. for 1 hour, resulting in white crystals. The crystals are recovered by filtration and dissolved in a mixed solution of 400 ml of water and 50 ml of a 40% NaOH solution, followed by extracting with 500 ml of chloroform. After washing the extract with 400 ml of water, the chloroform layer is dried over anhydrous magnesium sulfate, and the solvent is distilled off under reduced pressure for concentration. Distillation of the resultant residue yields 23 g of 2-methyl-3-chloroaniline as the fraction of 115°–116° C./10 mmHg.

REFERENCE EXAMPLE 2

Synthesis of N-ethyl-2-methyl-3-chloroaniline

In 100 ml of benzene is dissolved 14 g of 2-methyl-3-chloroaniline obtained in Reference Example 1 and, after adding 12 g of triethylamine, 13 g of ethyl bromide is added to the solution to conduct the reaction under reflux of benzene for 3 hours. After the completion of the reaction, the mixture is cooled to room temperature and shaken with 200 ml of water. The benzene layer is separated, dried over anhydrous magnesium sulfate, and concentrated. Distillation of the residue results in 12 g of N-ethyl-2-methyl-chloroaniline as the fraction of 125°–126° C./10 mmHg.

EXAMPLE 1

Synthesis of 1-ethyl-7-chloro-8-methyl-4-oxo-1,4-dihydroquinoline-3-carboxylic acid Ten grams of N-ethyl-2-methyl-3-chloroaniline is allowed to react with 15 g of diethyl ethoxymethylenemalonate under heating at 110° C. for 30 minutes. Then, polyphosphoric acid (obtained from 50 g each of phosphoric acid and phosphorus pentaoxide) is added to be subjected to the reaction at 140° C. for 40 minutes. After the reaction, the mixture is poured into 600 g of water and ice, resulting in crystals separated out. The crystals are recovered by filtration, and a 10% sodium hydroxide solution is added to the fitrate and the mixture is refluxed for 1 hour. After refluxing, the mixture is treated with activated carbon and adjusted to pH 2 with concentrated hydrochloric acid, whereby there separate out light yellow crystals. Recrystallization from dimethylformamide yields 11 g of 1-ethyl-7-chloro-8-methyl-4-oxo-1,4-dihydroquinoline-3-carboxylic acid as the white, needle-like crystals. mp. 221°–222° C.

EXAMPLE 2

Synthesis of 1-ethyl-7-fluoro-8-methyl-4-oxo-1,4-dihydroquinoline-3-carboxylic acid Nine grams of N-ethyl-2-methyl-3-fluoroaniline is allowed to react with 15 g of diethyl ethoxymethylenemalonate under heating at 110° C. for 30 minutes. Then, polyphosphoric acid (obtained from 50 g each of phosphoric acid and phosphorus pentaoxide) is added to be subjected to the reaction at 140° C. for 40 minutes. After the reaction is completed, the mixture is poured into 600 g of water and ice to obtain crystals. The crystals are recovered by filtration, and a 10% sodium hydroxide solution is added to the filtrate and the mixture is refluxed for 1 hour. After refluxing, the reaction mixture is treated with activated carbon and adjusted to pH 2 with concentrated hydrochloric acid, whereby there separate out light yellow crystals. Recrystallization from dimethylformamide yields 10 g of 1-ethyl-7-fluoro-8-methyl-4-oxo-1,4-dihydroquinoline-3-carboxylic acid as the white, needle-like crystals. mp. 245°–246° C.

EXAMPLE 3

Synthesis of 1-ethyl-7-(1-piperazinyl)-8-methyl-4-oxo-1,4-dihydroquinoline-3-carboxylic acid One hundred milliliter of hexamethylphosphoramide is added to a mixture of 5 g of 1-ethyl-7-chloro-8-methyl-4-oxo-1,4-dihydroquinoline-3-carboxylic acid and 8.5 g of anhydrous piperazine, and the mixture is heated at 140° C. for 8 hours. After heating, the solvent is removed under reduced pressure and, after 500 ml of water is added to the resultant residue, the mixture is adjusted to pH 4 with glacial acetic acid and the insolubles are filtered out. The filtrate is concentrated under reduced pressure, resulting in a light yellow, solid substance. Recrystallization from isopropanol-water (2:1) mixture yields 3.2 g of 1-ethyl-7-(1-piperazinyl)-8-methyl-4-oxo-1,4-dihydroquinoline-3-carboxylic acid hydrochloride as the white, needle-like crystals. m.p. not less than 300° C.

Elementary analysis (for $C_{17}H_{21}O_3N_3HCl.H_2O$)

|  | C | H | N |
|---|---|---|---|
| Calcd. (%): | 55.16 | 6.49 | 11.35 |
| Found (%): | 55.03 | 6.39 | 11.28 |

PREPARATION EXAMPLE 1

| The compound obtained in Example 3; | 200 mg |
| Glucose; | 250 mg |
| Distilled water for injection; | Suitable amount |
| The total amount | 5 ml |

In distilled water for injection are dissolved the compound of this invention and glucose, and the solution is filled in an ampoule with a 5 cc content, which, after being replaced with nitrogen, is sterilized under pressure at 121° C. for 15 minutes. By this procedure, there is obtained an injection preparation of the composition described above.

PREPARATION EXAMPLE 2

| | |
|---|---|
| The compound obtained in Example 3; | 100 g |
| Abishell (tradename, product of Asahi Chemical Industry, Japan); | 40 g |
| Corn starch | 30 g |
| Magnesium stearate | 2 g |
| TC-5 (tradename, product of Shin-estu Chemical Co., Japan; hydroxypropyl-methylcellulose); | 10 g |
| Polyethylene glycol-6000 | 3 g |
| Castor oil | 40 g |
| Methanol | 40 g |

The compound of this invention, Abishell, corn starch and magnesium stearate are weighed out, mixed, milled and compressed into tablets by the use of punches, "Sugar-Coat R 10 mm". The resultant tablets are coated with the film coating agent composed of TC-5, polyethylene glycol-6000, castor oil and methanol to thereby produce the film-coated tablets having the composition described above.

PREPARATION EXAMPLE 3

| | |
|---|---|
| The compound obtained in Example 3; | 2 g |
| Anhydrous lanolin; | 5 g |
| Bleached beewax; | 5 g |
| White petrolatum | 88 g |
| Total amount | 100 g |

Bleached beewax is warmed to a liquid form, and the compound of this invention, anhydrous lanolin and white petrolatum are added. The mixture is warmed to become liquid. Stirring is continued until the mixture starts to solidify, and there is obtained the ointment of the above-mentioned composition.

PREPARATION EXAMPLE 4

| | |
|---|---|
| Sodium salt of the compound obtained in Example 1; | 20 g |
| Talc; | 980 g |

The compound of this invention and talc are mixed and milled, resulting in powders.

PREPARATION EXAMPLE 5

| | |
|---|---|
| The compound obtained in Example 1 | 200 g |
| White carbon; | 20 g |
| Sodium lignin sulfonate | 20 g |
| Polyoxyethylene alkyl ether | 40 g |
| Clay | 720 g |

The above compounds are mixed and milled to produce wettable powders.

PREPARATION EXAMPLE 6

| | |
|---|---|
| The compound obtained in Example 1; | 100 g |
| Diatomaceous earth; | 210 g |
| Talc | 200 g |
| Sodium alkyl sulfate | 90 g |

The above compounds are mixed and milled to produce wettable powders.

PREPARATION EXAMPLE 7

| | |
|---|---|
| The compound obtained in Example 1; | 100 g |
| Talc | 380 g |
| Clay | 370 g |
| Bentonite | 100 g |
| Sodium alkyl sulfate | 50 g |

The above compounds are mixed, milled and then granulated by a granulating machine to produce granules.

ANTIMICROBIAL-ACTIVITY TEST 1

For two of the compounds of this invention and 1-ethyl-1,4-dihydro-7-methyl-4-oxo-1,8-naphthylidene-3-carboxylic acid (nalidixic acid employed as the control compound), the antimicrobial activities against various microorganisms were determined by the agar dilution plate method. The minimal inhibitory concentrations obtained against the microorganisms are shown in Table 1. In this test, each of the test microorganisms was prepared at $1 \times 10^8$ cells/ml (O.D.660 m$\mu$, 0.13–0.14) and $1 \times 10^6$ cells/ml.

TABLE 1

| | Minimal inhibitory concentration, $\mu$g/mg | | | | | |
|---|---|---|---|---|---|---|
| | Compound 1* | | Compound 2* | | Control compound | |
| Test microorganisms | $1 \times 10^8$ | $1 \times 10^6$ | $1 \times 10^8$ | $1 \times 10^6$ | $1 \times 10^8$ | $1 \times 10^6$ |
| Staphylococcus aureus FDA 209P | 6.3 | 3.1 | 1.6 | 1.6 | 50 | 50 |
| Streptococcus pyogenes IDS-23 | 25 | 12.5 | 100 | 100 | >100 | >100 |
| Escherichia coli NIHI | 6.3 | 3.1 | 0.4 | 0.1 | 3.1 | 1.6 |
| Klebsuekka pneumoniae | 1.6 | 0.8 | 0.8 | 0.8 | 1.6 | 0.4 |
| Preteus rettgeri HIH 96 | 0.8 | 0.8 | 0.1 | 0.1 | 0.8 | 0.8 |
| Salmonella typhi O-901 | 0.4 | 0.4 | 0.4 | 0.4 | 3.1 | 1.6 |
| Shigella sonnei EW-33 | 6.3 | 3.1 | 0.8 | 0.4 | 3.1 | 1.6 |
| Serratia marcescens IFO 12648 | 1.6 | 3.1 | 0.8 | 0.8 | 6.3 | 6.3 |
| Pseudomonas aeruginosa E-2 | 12.5 | 12.5 | 25 | 12.5 | >100 | 100 |
| Ps. aeruginosa NCTC 10490 | 6.3 | 3.1 | 12.5 | 6.3 | 50 | 25 |
| Ps. aeruginosa ATCC 10145 | 12.5 | 6.3 | 25 | 12.5 | >100 | >100 |

Remarks:
*; Compound 1 = 1-ethyl-7-(1-piperazinyl)-8-methyl-4-oxo-1,4-dihydroquinoline-3-carboxylic acid.
Compound 2 = 1-ethyl-7-chloro-8-methyl-4-oxo-1,4-dihydroquinoline-3-carboxylic acid.

ANTIMICROBIAL-ACTIVITY TEST 2

The compound of this invention is brought into a 2% acetone solution, which is, then, diluted with water to the desired concentration. 1 ml each of the solutions of various concentrations is placed in a Petri dish, and mixed with 9 ml of the potato-dextrose-agar medium (referred to as PDA medium) to prepare a agar plate for various concentrations of each of the above-mentioned test compounds.

The minimal inhibitory concentration against various bacteria were determined by the agar dilution plate method. In fungi, a test microorganism cultured in advance in a PDA medium is stamped out on the front end by a cork borer having a diameter of 10 mm to thereby prepare a disc of the fungal mmycelia, and such disc is placed, with the mycelia surface down, on each of the agar plates as prepared by the above-mentioned procedure.

By observing with the naked eye 2 days later whether there is further growth of the mycelia, determined is the minimal inhibitory concentration to inhibit completely the growth of the mycelia, and the minimal inhibitory concentrations as obtained for test microorganisms are shown in Table 2, whereby the test microorganisms employed are described below in parentheses, together with the names of plant diseases:

A: Soft rot of vegetable (*Erwinia carotovora*)
B: Bacterial blight of rice (*Xanthomonas oryzae*)
C: Peach bacterial spot (*Xanthomonas pruni*)
D: Citrus canker (*Xanthomonas citri*)
E: Baceterial wilt of tomato (*Pseudomonas solanacearum*)
F: Angular leaf spot of cucumber (*Pseudomonas lachrymans*)
G: Rice blast disease (*Pyrisularia oryzae*)
H: Helminthosporium leaf spot (*Helminthosporium oryzae*)
I: Late blight of cucumber (*Phytophthora melonis*)
J: Leaf blight of cucumber (*Phytophthora capsici*)
K: Anthracnose of cucumber (*Colletotrichum lagenarium*)
L: Stem rot of eggplant (*Sclerotinia sclerotiorum*)
M: Gammy stem blight of melon (*Mycosphaerella melonis*)
N: Early blight of tomato (*Alternaria solani*)

TABLE 2

| Test microorganism | | Minimum inhibitory concentration for the compound 2, μg/ml |
|---|---|---|
| Bacteria (10⁸ cells/ml) | A | 0.2 |
| | B | 0.2 |
| | C | 0.4 |
| | D | 0.1 |
| | E | 0.1 |
| | F | 100 |
| Fungi | G | 50 |
| | H | 50 |
| | I | 12.5 |
| | J | 25 |
| | K | 100 |
| | L | 100 |
| | M | 50 |
| | N | 50 |

ANTIMICROBIAL-ACTIVITY TEST 3

A disk of a Japanese radish, cut to a size of 2 cm in diameter and 1 cm in height, is punched on the central portion. The disc of a Japanese radish is soaked for 1 hour in a solution of a drug prepared to the desired concentration, and air-dried. The disk of a Japanese radish is inoculated on the damaged central portion with 10 μl of a suspension of *Erwinia carotovora* (soft-rot causing bacterium, about 10⁸ cells/ml) and maintained in the humid state at 28° C. Investigation on the incidence of the soft rot is made 24 hours later.

The incidence index is determined as follows:

| Ratio of diseased area | Disease incidence index |
|---|---|
| 0 | 0 |
| 0< ≦⅓ | 1 |
| ⅓< ≦⅔ | 2 |
| >⅔ | 3 |

Test results obtained with the compound 2 and control are shown in Table 3.

TABLE 3

| Test compound | Concentration, μg/ml | Number of test specimens | | | | |
|---|---|---|---|---|---|---|
| | | 1 | 2 | 3 | 4 | 5 |
| Compound 2 | 125 | 0 | 0 | 0 | 0 | 1 |
| | 62.5 | 0 | 0 | 0 | 0 | 1 |
| | 31.3 | 0 | 0 | 0 | 1 | 1 |
| | 15.6 | 0 | 1 | 1 | 1 | 1 |
| Control (Streptomycin) | 125 | 1 | 1 | 1 | 1 | 1 |
| | 62.5 | 1 | 1 | 2 | 2 | 2 |
| | 31.3 | 2 | 2 | 3 | 3 | 3 |
| | 15.6 | 3 | 3 | 3 | 3 | 3 |
| Non-treated | 0 | 3 | 3 | 3 | 3 | 3 |

DATA ON ACUTE TOXICITY

An acute toxicity test was conducted by administering orally the Compounds 1 and 2 as hereinbefore described to rats (Wister strain, male). The estimated $LD_{50}$ values of both of the Compounds 1 and 2 were not less than 500 mg/kg.

What is claimed is:

1. A quinoline carboxylic acid derivative represented by the formula

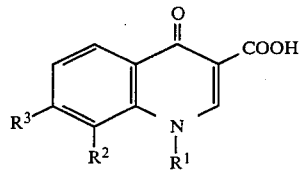

wherein $R^1$ is ethyl, $R^2$ is methyl and $R^3$ is chlorine or fluorine and its pharmacologically or agrochemically acceptable salt.

2. A quinoline carboxylic acid derivative and its pharmacologically or agrochemically acceptable salt as defined in claim 1, wherein said quinoline carboxylic acid derivative is 1-ethyl-7-chloro-8-methyl-4-oxo-1,4-dihydroquinoline-3-carboxylic acid.

3. A quinoline carboxylic acid derivative and its pharmacologically or agrochemically acceptable salt as defined in claim 1, wherein said quinoline carboxylic acid derivative is 1-ethyl-7-fluoro-8-methyl-4-oxo-1,4-dihydroquinoline-3-carboxylic acid.

* * * * *